United States Patent [19]
Goldstein et al.

[11] Patent Number: 5,547,670
[45] Date of Patent: Aug. 20, 1996

[54] RECOMBINANT HYBRID PORIN EPITOPES

[75] Inventors: Neil I. Goldstein, West Orange, N.J.; Charles T. Tackney, Brooklyn, N.Y.

[73] Assignee: Imclone Systems Incorporated, New York, N.Y.

[21] Appl. No.: 124,369

[22] Filed: Sep. 20, 1993

Related U.S. Application Data

[63] Continuation of Ser. No. 669,528, Mar. 14, 1991, abandoned.

[51] Int. Cl.$^6$ .......................... C12N 15/62; C12N 15/70; C07K 14/22
[52] U.S. Cl. ...................... 424/192.1; 424/190.1; 424/200.1; 424/278.1; 424/249.1; 530/300; 530/350
[58] Field of Search ................ 424/192.1, 249.1, 424/190.1, 200.1, 278.1, 185.1; 530/350, 300; 435/69.3, 172.3, 252.33

[56] References Cited

FOREIGN PATENT DOCUMENTS

WO89/04873  1/1989  WIPO .............. C12P 21/00

OTHER PUBLICATIONS

Hopp et al Proc Natl Acad Sci USA vol. 78 pp. 3824–3828 (1981).
Kyle et al, J Mol Biol. vol. 157, pp. 105–132 (1982).
Sambrook et al Moleculer Cloning, A Laboratory Manual 2nd Edition Cold Spring Herbor Laboratory, CSH, NY (1989) Ch 17.
Carbanelti et al Proc Natl Acad Sci USA vol. 85 pp. 6841–6845 (1988).
Carbanetti et al Proc Natl Acad Sci USA vol. 84 pp. 9084–9088 (1987).
Fletcher et al Journal of Gen Microbio vol. 132 pp. 1611–1620 (1986).
Rajasekariah et al., Journal of Clinical Microbiology, Jul. 1989, 1700–1703.
Joiner et al., Journal of Immunology, 134 (5), 3411–3419 (1985).
Virji et al., Journal of General Microbiology, 133, 2639–2646 (1987).
Gotschlich et al., Proc. Natl. Acad. Sci. USA, 84, 8135–8139 (1987).
Virji et al., Journal of General Microbiology, 133, 2639–2646 (1987).
Gotschlick et al., Proc. Natl. Acad. Sci. USA, 84, 8135–8139 (1987).
Shinners and Catlin, The Journal of Infectious Disease, vol. 158, No. 3, Sep. 1988.
Heckels et al., Journal of General Microbiology, 135, 2269–2276 (1989).
Berzofsky, Science vol. 229 pp. 932–940 (1985).
Gennaro, A. R. Remington's Pharmaceutical Science, Eighteenth Edition, published 1992 by Mack Publishing Co. (Easton, Pa.) Chap. 72 pp. 1389–1404.

*Primary Examiner*—Christine M. Nucker
*Assistant Examiner*—Laurie Scheiner
*Attorney, Agent, or Firm*—Irving N. Feit; Thomas C. Gallagher

[57] ABSTRACT

The present invention provides a polypeptide that is nontoxic in *E. coli*. The disclosed polypeptide comprises at least one antigenic sequence present in P.IA of *N. gonorrhoeae* and at least one antigenic sequence present in P.IB of *N. gonorrhoeae*. Further, the disclosed polypeptide of the invention is fused to a carrier peptide.

4 Claims, 8 Drawing Sheets

Figure 1A

| | | Amino Acids |
|---|---|---|
| P.IA Fragments | | |
| 1. | DVTLYGTIKAGVETSRSVAHHGAQAD | 1-26 |
| 2. | VETSRSVAHHGAQADRVKTATEIAD | 12-36 |
| 3. | DTGGFNPWEGKSYYLGLSNIAQPEERHV | 99-126 |
| 4. | FVQYAGFYKRHSYTTEKHQVHRLVG | 169-193 |
| P.IB Fragments | | |
| 5. | GAIKAGVQTYRSVEHTDGKVSKVETGS | 6-32 |
| 6. | GLFQRYGEGTKKIEYEHQVYSIPSLFV | 178-204 |

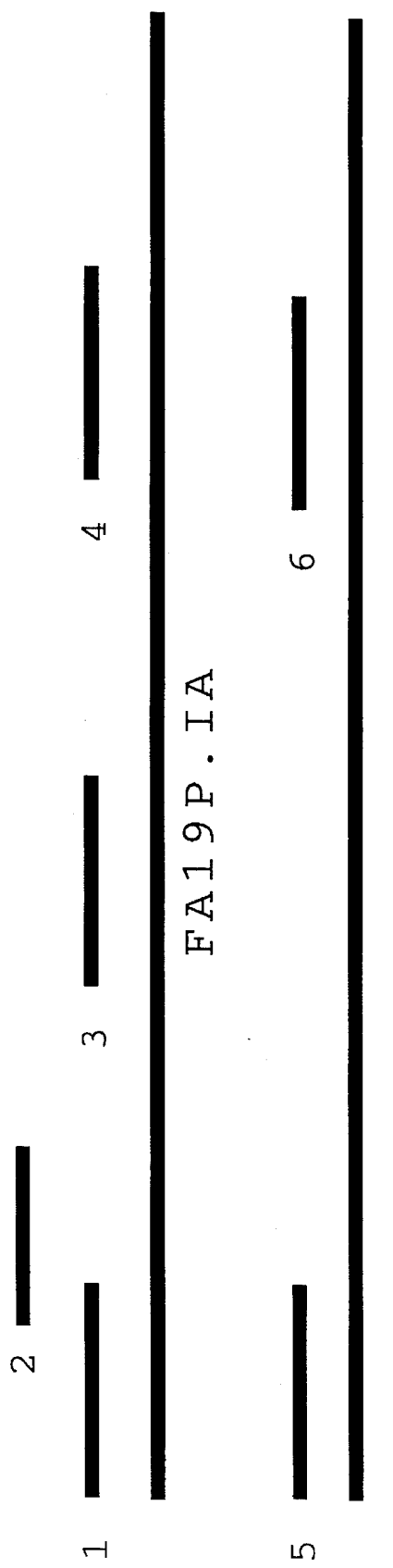

Figure 2

ATT GAG ATC CCC CCG AAT TGG GAA TTC GAG CTC GGT ACC CGG 42

GGA TCC TCT AGA GTC GAC CTC GAC CTC CAG GCA TGC AAG CTT 78

Figure 4A (g) 5' CATTCCGAGCCTGTGTTTGTTTTCGTTCAGTACGCTGGTTTCTAC 3'

(h) 5' ACGTTTGTAGAAACCAGCGTACTGAACGAAAACAAACAFGCTCGGAATGCT 3'

(i) 5' AAACCTCACTCCTACACCGAAAAACACCAGGTTCACCGTCTGGTTGGTTA 3'

(j) 5' AGCTTAACCAACCAGACGGTGAACCTGGTCTTTTTCGGTGGTGTAGGAGTG 3'.

Figure 5

```
AATTCGATG ATGACGATAA AGTAGAAACT TCCCGCTCCG TAGCTCACCA     50
      GCTAC TACTGCTATT TCATCTTTGA AGGGCGAGGC ATCGAGTGGT

TGGAGCTCAG GCGGATCGCG TTAAAACCGC TACCGAAATC GCTGATTTGG    100
ACCTCGAGTC CGCCTAGCGC AATTTTGGCG ATGGCTTTAG CGACTAAACC

GCTTGTTCCA AAGATACGGC GAAGGCACTA AAAAAATCGA ATACGAACAT    150
CGAACAAGGT TTCTACGCCG CTTCCGTGAT TTTTTTAGCT TATGCTTGTA

CAAGTTTATA GTATCCCCAG CCTGTTTGTT TAAA                     184
GTTCAAATAT CATAGGGGTC GGACAAACAA ATTTTCGA
```

RECOMBINANT HYBRID PORIN EPITOPES

"This application is a continuation application of Ser. No. 07/669,528, filed Mar. 14, 1991, which is now abandoned" as the first sentence of the specification.

The diseases caused by the gonococcus *Neisseria gonorrhoeae*, such as gonorrhea, are among the most prevalent venereal diseases in the world. Such diseases have proven to be difficult to control by traditional antibiotic and vaccine treatments.

In PCT application WO 89/04873, Carbonetti and Sparling describe an approach to vaccines based on a porin protein present in the outer membrane of *N. gonorrhoeae*. This protein, which is called protein I, forms pores that allow small hydrophilic solutes to pass through the outer membrane. Protein I (P.I) may be divided into two genetically and immunologically distinct serovar groups present in *N. gonorrhoeae*, P.IA and P.IB.

The DNA sequence of the P.I gene of FA19, a IA serovar, is shown as FIG. 3 of WO 89/04873. The DNA sequence of the PI gene of MS11, a IB serovar, is shown as FIG. 9 of WO 89/04873. The DNA sequences shown in FIGS. 3 and 9 as well as the corresponding amino acid sequences, which are also shown, are incorporated herein by reference. The DNA sequence of the PI gene of R10, a IB serovar, and the corresponding amino acid sequence is disclosed by Gotschlich et al. in Proc. Nat'l Acad. Sci. USA 84, 8135–8139 (1987). The DNA and amino acid sequences of P.IB as reported by Gotschlich et al. are incorporated herein by reference.

Successful approaches to the prevention, detection and treatment of gonococcal infection must be directed to both of the clinically important *N. gonorrhoeae* serovar groups. One approach to solving this problem is the development of intertypic hybrids. Such hybrids are generally prepared by inserting a selectable marker into the DNA of a strain of one serovar, and transfecting the DNA into a strain of the other serovar. Random recombination of the largely homologous P.I genes in the transfected cell leads to a hybrid gene that expresses some epitopes of both P.IA and P.IB. Such intertypic hybrids have been described by Carbonetti and Sparling in PCT application WO 89/04873 and by Shinners and Catlin in J. Infect. Dis. 158, 529–536 (1988).

One difficulty with the intertypic hybrid approach is that the recombinant porin proteins are full length P.I proteins, which have approximately 300 amino acids. Such proteins are difficult to work with due to poor solubility, and to be produced by genetic engineering methods in *E. coli* due to toxicity problems. The difficulty of growing large numbers of porin gene-containing bacterial cells has been described by Gotschlich et al in Proc. Nat'l Acad. Sci USA 84, 8135–8139)1987) and Carbonetti and Sparling, PCT application WO 89/04873.

Moreover, intertypic hybrids result from random recombination events, and do not constitute a rational approach to the design of a protein useful in diagnostic methods, vaccines and treatments of diseases caused by *N. gonorrhoeae*. One hopes to do better than to have to pick and choose among various randomly formed proteins to determine which, if any, might be useful.

There is a need, therefore, for rationally designed chimeric proteins that contain epitopes of both P.IA and P.IB. There is a particular need for such chimeric protein that are not toxic to *E. coli*, and that have fewer than 300 amino acids.

SUMMARY OF THE INVENTION

These and other objectives as will be apparent to those having ordinary skill in the art have been met by providing a polypeptide that is non-toxic in *E. coli*. The polypeptide comprises at least one antigenic sequence present in P.IA of *N. gonorrhoeae* and at least one antigenic sequence present in P.IB of *N. gonorrhoeae*.

The invention further relates to a polypeptide comprising at least one antigenic sequence present in P.IA of *N. gonorrhoeae* and at least one antigenic sequence present in P.IB of *N. gonorrhoeae*. The total number of amino acids in the antigenic sequence present in P.IA is no more than 125. The total number of amino acids in the antigenic sequence present in P.IB is also no more than 125.

DESCRIPTION OF THE FIGURES

FIG. 1A shows the antigenic sequences corresponding to P.I fragments 1–6 (SEQ ID NOS:1–6). Each fragment optionally contains an additional N-terminal cysteine residue. The amino acid numbers correspond to the amino acid residues of P.IA from *N. gonorrhoeae* strain FA19 (fragments 1–4 (SEQ ID NOS:1–4)) or of P.IB from *N. gonorrhoeae* strain MS11 (fragments 5 and 6 (SEQ ID NOS:5–6)).

FIG. 1B shows the relative positions of fragments 1–4 (SEQ ID NOS:1–4) on P.IA from *N. gonorrhoeae* strain FA19 and fragments 5 and 6 (SEQ ID NOS:5–6) on P.IB from *N. gonorrhoeae* strain MS11.

FIG. 2 shows the nucleotide sequence of the polylinker in PATH20 (SEQ ID NO:7).

FIG. 4A shows the nucleotide sequence of the four oligonucleotides (g–j (SEQ ID NOS:10–13)) used to prepare a chimeric polypeptide containing fragments 2, 6, and 4 called GC264.

FIG. 5 shows the nucleotide sequence (SEQ ID NOS:14–15) used to express GC26 in bacteria (see Example 1).

DETAILED DESCRIPTION

Fragments

Figure 3A:
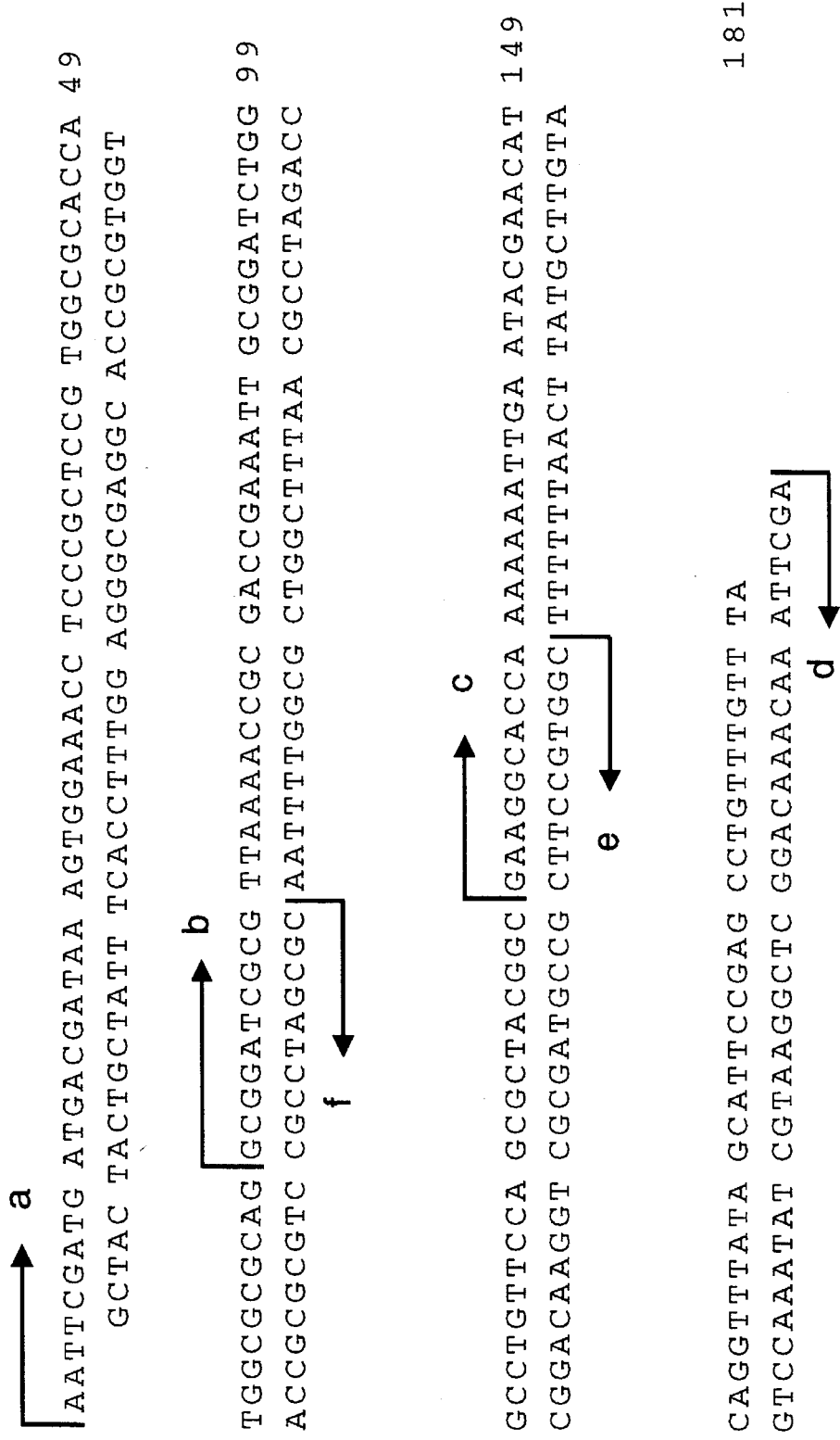
FIG. 3A shows the nucleotide sequence of the six oligonucleotides (a–f (SEQ ID NOS:8–9)) used to prepare a chimeric polypeptide containing fragments 2 and 6 called GC26 (see Example 1).

The invention relates to chimeric polypeptides comprising fragments containing antigenic sequences of both P.IA and P.IB from an *N. gonorrhoeae* strain of a IA or IB serovar, respectively. Strains of both serovar groups IA and IB are known. Some known IA strains include, for example, FA19, FA6599, FA6642, NRL V.15, NRL 7929, and NRL G.7. Some strains of the IB serovar include, for example, MS11, R10, NRL T.13, NRL1955, NRL5767, 4403(Pgh3-2), 4408(Pgh3-1), and 4409(51288).

Fragments containing antigenic sequences of P.IA and P.IB may be selected on the basis of generally accepted criteria of potential antigenicity and/or exposure. Such criteria include the hydrophilicity and relative antigenic index, as determined by surface exposure analysis of P.IA and P.IB proteins. The determination of appropriate criteria is known to those skilled in the art, and has been described, for example, by Hopp et al, Proc. Nat'l Acad. Sci. USA 78, 3824–3828 (1981); Kyte et al, J. Mol. Biol. 157, 105–132

(1982); Emini, J. Virol. 55, 836–839 (1985); Jameson et al, CA BIOS 4, 181–186 (1988); and Karplus et al, Naturwissenschaften 72, 212–213 (1985). Amino acid domains predicted by these criteria to be surface exposed are selected preferentially over domains predicted to be more hydrophobic or hidden.

Fragments 1–6 (SEQ ID NOS:1–6), which are shown in FIG. 1A, are suitable antigenic sequences. Fragments 1–4 (SEQ ID NOS:1–4) contain amino acid sequences found in P.IA of gonococcal strain FA19. Fragments 5 and 6 (SEQ ID NOS:5–6) contain amino acid sequences found in P.IB of gonococcal strain MS11. These fragments were disclosed in a simultaneously-filed continuation-in-part of a U.S. patent application of Carbonetti and Sparling having Ser. No. 07/242,758, which is equivalent to WO 89/04873.

Chimeric polypeptides

The chimeric polypeptides of the present invention comprise at least two fragments. At least one fragment comprises an antigenic sequence present in P.IA of N. gonorrhoeae. At least one other fragment comprises an antigenic sequence present in P.IB of *N. gonorrhoeae.*

In addition, the chimeric polypeptides of the invention satisfy certain immunological criteria. First, the polypeptides bind to monoclonal and polyclonal sera specific to type IA and IB porin serovars of *N. gonorrhoeae*, as well as to monoclonal and polyclonal antibodies specific to each individual fragment of the chimeric polypeptide. In addition, the chimeric polypeptides illicit specific serum antibody responses in mammals, including humans, toward at least one epitope of both a type A and a type B serovar.

Any rationally designed chimeric polypeptide that has at least two antigenic sequences, at least one of which is present in P.IA and at least one other of which is present in P.IB of *N. gonorrhoeae*, and that satisfies the immunological criteria described above, may be used in the invention. As used in this specification, the term "chimeric polypeptide" means a polypeptide that has a rationally designed amino acid sequence, as opposed to the sequences of the randomly formed intertypic hybrids of the prior art.

In a preferred embodiment of the invention, the chimeric polypeptide comprises at least one polypeptide fragment selected from P.IA fragments 1–4 (SEQ ID NOS:1–4) joined to at least one polypeptide fragment selected from P.IB fragments 5 and 6 (SEQ ID NOS:5–6). The order in which the fragments occur in the polypeptide is not critical, as long as at least one P.IA fragment and at least one P.IB fragment remains antigenic. Some examples of chimeric polypeptides in accordance with the invention comprise fragments 2-6, 6-2, 4-5, 5-4, 1-6, 6-1, 2-6-4, 2-4-6, and 2-5-6. Chimers formed by fragments 2 and 6 and by fragments 2, 4, and 6 are preferred.

The fragments of the invention, such as fragments 1–6, are preferably highly hydrophilic and, therefore, predictably immunologically valid. Each fragment comprises at least one P.I epitope. Preferably, each fragment contains more than one P.I epitope.

The antigenic fragments of the chimeric polypeptide may be sub-fragments of fragments 1–6 (SEQ ID NOS:1–6), and contain less than all of the epitopes of its respective fragment. The fragment may have as few as one epitope. For example, a known epitope of fragment 6 is YSIPS.

Alternatively, some or all of the antigenic P.IA and/or P.IB sequences are not those represented by fragments 1–6 (SEQ ID NOS:1–6). These other fragments may or may not overlap fragments 1–6 (SEQ ID NOS:1–6).

The fragments of the chimeric polypeptide may contain additional amino acid sequences at either their N- or C-terminal or at both termini. These additional amino acid sequences may be present in P.IA or P.IB. Alternatively, the additional amino acid residues may be derived from proteins other than P.IA or P.IB. Such additional amino acid residues may aid in the isolation and purification of the polypeptide, aid in the presentation of the antigenic sequences to a host, or otherwise enhance the immunological properties of the polypeptides.

The additional amino acids are preferably separated from the P.IA/P.IB antigenic fragments by a suitable cleavage site. Both chemical and enzymatic cleavable sites are known in the art. Suitable examples of sites that are cleavable enzymatically include sites that are specifically recognized and cleaved by collagenase (Keil et al., FEBS Letters 56, 292–296 (1975)); enterokinase (Hopp et al., Biotechnology 6, 1204–1210 (1988)); factor Xa (Nagai et al., Methods Enzymol. 153, 461–481 (1987)); and thrombin (Eaton et al., Biochemistry 25, 505 (1986)). Collagenase cleaves between proline and X in the sequence Pro-X-Gly-Pro wherein X is a neutral amino acid. Enterokinase cleaves after lysine in the sequence Asp-Asp-Asp-Asp-Lys. Factor Xa cleaves after arginine in the sequence Ile-Glu-Gly-Arg. Thrombin cleaves between arginine and glycine in the sequence Arg-Gly-Ser-Pro.

Specific chemical cleavage agents are also known. For example, cyanogen bromide cleaves at methionine residues in proteins.

The chimeric polypeptide should be as short as possible. Unnecessary amino acids add to the length of the polypeptide, and to the difficulty of working with it. Therefore, although additional amino acid sequences may be present at the N-terminal or C-terminal end of a fragment or between the fragments, the chimeric polypeptide preferably contains no additional amino acid sequences other than the antigenic fragments from a P.I protein, such as fragments 1–6 (SEQ ID NOS:1–6).

The fragments are preferably identical to sequences in a strain of *N. gonorrhoeae*. It is, however, possible to create an equivalent fragment by deleting amino acids from a fragment without affecting all or any of the epitopes.

As is also known, it is possible to substitute amino acids in a sequence with equivalent amino acids. Groups of amino acids known normally to be equivalent are:

(a) Ala(A) Ser(S) Thr(T) Pro(P) Gly(G);

(b) Asn(N) Asp(D) Glu(E) Gln(Q);

(c) His(H) Arg(R) Lys(K);

(d) Met(M) Leu(L) Ile(I) Val(V); and (e) Phe(F) Tyr(Y) Trp(W).

Substitutions, additions and/or deletions in the antigenic sequences may be made as long as the chimeric polypeptide of the invention continues to satisfy the immunological criteria described above. An amino acid sequence that is substantially the same as another sequence, but that differs from the other sequence by means of one or more substitutions, additions and/or deletions is considered to be an equivalent sequence. Preferably, less than 25%, more preferably less than 10%, of the number of amino acid residues in a P.IA or P.IB sequence are substituted for, added to, or deleted from the fragments in the chimeric polypeptides of the invention.

By limiting the number of amino acids, the solubility and ease of handling of the chimeric polypeptides are increased. Preferably, the total number of amino acids in the P.IA antigenic sequence or sequences, or equivalent sequence or sequences, in the chimeric polypeptide is no more than about 125, preferably no more than about 75, and more preferably no more than about 50. Similarly, the total number of amino acids in the P.IB antigenic sequence or sequences, or equivalent sequence or sequences, in the chimeric polypeptide is also no more than about 125, preferably no more than about 75, and more preferably no more than about 50.

Preferably, the chimeric porin polypeptides of the invention, unlike the P.IA, P.IB and P.IA/B intertypic hybrids of the prior art, are non-toxic in *E. coli*. Toxic proteins do not generally allow binary growth of the organism to high absorbance at 650 nm or to high cell number. Absorbance at 650 nm, a reflection of total cell number and therefore cell mass, should continue to rise exponentially throughout the growth period until media exhaustion and plateau growth. Chemostatic or media supplemented growth should occur throughout the entire incubation growth phase without cell lysis or death. Cellular product, i.e., fusion protein, should accumulate steadily following induction (i.e., IAA, IPTG, 42° C., etc.) and allow product to be gathered after overnight shake culture growth. Typical 650 nm absorbance values of 5–10 units are obtained in shake flasks or 25–100 units in media supplemented chemostat environments. There should be no inflection of the growth curve representing premature cell lysis during the growth cycle. The failure to achieve sufficiently high cell mass or $A^{650\ nm}$ absorbance precludes economically efficient industrial scale production.

To be considered non-toxic in *E. coli* means that the protein is non-lytic in *E. coli* when it is expressed under normal conditions. To be expressed under normal conditions means that unusual steps are not taken in order to be able to express toxic proteins in *E. coli*.

Unusual steps include the use of highly individual and transient systems such as the T7 promoter/polymerase system of Studier (Studier and Moffatt in J. Mol. Biol. 189, 113–130 (1986) and Moffatt and Studier, Cell 49, 221–227 (1987)), and the use of specific and generally unavailable *E. coli* host cells (e.g. BL21 pLys, etc.) or expression plasmids. Unusual methods may require the halting of growth and gathering of cell mass at relatively low $A^{650}$ levels in order to avoid premature cell lysis and death and the possibility of product destruction.

Normal conditions for expression of a protein in *E. coli* include the use of standard vector systems or generally available promoter cassettes (Trp, Tac, Trc, lambda P, beta-gal, etc.) in standard media components and during continuous growth to high cell mass and/or $A^{620}$ values. Cell growth should occur continuously with media replacement or chemostatic growth with no premature lysis, increase in lysis-generated viscosity, or sudden drop in $A^{620}$ upon continuous post-induction shaker or fermenter growth. Subsequent plasmid stability should remain high upon continuous growth and polypeptide production.

Synthesis of Chimeric Polypeptides

The chimeric fragments may be synthesized from individual amino acid residues by methods known in the art. Some suitable methods are described by Stuart and Young in "Solid Phase Peptide Synthesis," Second Edition, Pierce Chemical Company (1984).

The proteins of the present invention are preferably produced by means of recombinant DNA technology. General methods for producing recombinant proteins from isolated DNA are described by Sambrook et al, in "Molecular Cloning," Second ed Cold Spring Harbor Press (1987).

Briefly, DNA coding for the desired amino acid sequence of the present invention may be obtained as fragments from natural sources and, optionally, modified. The DNA may also be synthesized in whole or in part by methods known in the art. Such methods include those described by Caruthers in Science 230, 281–285 (1985).

The DNA encoding the desired polypeptide of the invention may be replicated using a wide variety of vectors in a wide variety of host cells. The host cells may be prokaryotic or eukaryotic. The vector may comprise segments of chromosomal, non-chromosomal and synthetic DNA sequences. Some suitable prokaryotic vectors include plasmids from *E. coli* such as colE1, pCR1, pBR322, pUC, pKSM, pMB9, and RP4. Prokaryotic vectors also include derivatives of phage DNA such as NM 989, M13 and other filamentous single-stranded DNA phages.

Vectors for expressing proteins in bacteria, especially *E. coli*, are also known. Such vectors include the PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. Other expression vector systems are based on beta-galactosidase (pEX) lambda $P_L$; maltoSe binding protein (pMAL); glutathione S-transferase (pGST)—see Gene 67, 31 (1988) and Peptide Research 3, 167 (1990).

Vectors useful in yeast are also available. A suitable example is the 2u plasmid.

Suitable vectors for use in mammalian cells are also known. Such vectors include well-known derivatives of SV-40, adenovirus, retrovirus-derived DNA sequences and vectors derived from combination of plasmids and phage DNA.

Further eukaryotic expression vectors are known in the art. See, for example, P. J. Southern and P. Berg, J. Mol. Appl. Genet. 1, 327–341 (1982); S. Subramani et al, Mol. Cell. Biol. 1, 854–864 (1981); R. J. Kaufmann and P. A. Sharp, "Amplification And Expression Of Sequences Cotransfected with A Modular Dihydrofolate Reductase Complementary DNA Gene," J. Mol Biol 159, 601–621 (1982); R. J. Kaufmann and P. A. Sharp, Mol. Cell. Biol. 159, 601–664 (1982); S. I. Scahill et al, "Expression And Characterization Of The Product Of A Human Immune Interferon DNA Gene In Chinese Hamster Ovary Cells," Proc. Natl. Acad. Sci. USA 80, 4654–4659 (1983); G. Urlaub and L. A. Chasin, Proc. Natl. Acad. Sci. USA 77, 4216–4220, (1980).

Useful expression hosts include well-known prokaryotic and eukaryotic hosts. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRCl, Pseudomonas, Bacillus, such as *Bacillus subtilis*, and Streptomyces. Suitable eukaryotic cells include yeasts and other fungi, insect, animal cells, such as COS cells and CHO cells, human cells and plant cells in tissue culture.

The expression vectors useful in the present invention contain at least one expression control sequence that is operatively linked to the desired DNA sequence. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The chimeric polypeptides may be purified by methods known in the art. Preferably, the polypeptides are isolated in an essentially pure state. A polypeptide is considered to be essentially pure if it is at least 85%, preferably at least 95%, and more preferably at least 99% pure. In one purification method, the chimeric polypeptide may be expressed in the form of a fusion protein with an appropriate fusion partner to facilitate purification and identification. Some useful fusion partners include maltose binding protein, Guan et al., Gene 67, 21–30 (1987); Maina et al., Gene 74, 36–373 (1988); Riggs, P., in Ausebel, F. M. et al (eds) Current Protocols in Molecular Biology, Greene Associates/Wiley Interscience, New York (1990); beta-galactosidase (Gray, et al., Proc. Natl. Acad. Sci. USA 79, 6598 (1982)); trpE (Itakura et al., Science 198, 1056 (1977)) protein A (Uhlen et al., Gene 23 369 (1983)) and glutathione S-transferase (Johnson, Nature 338, 585 (1989); and Van Etten et al., Cell 58, 669 (1989)).

Such fusion proteins may be purified by affinity chromatography using reagents that bind to the fusion partner. The reagent may be a specific ligand of the fusion partner or an antibody, preferably a monoclonal antibody. For example, fusion proteins containing beta-galactosidase may be purified by affinity chromatography using an anti-beta-galactosidase antibody column (Ullman, Gene. 29, 27–31 (1984)). Similarly, fusion proteins containing maltose binding protein may be purified by affinity chromatography using a column containing maltose.

Optionally, the DNA that encodes the fusion protein is engineered so that the fusion protein contains a cleavable site between the chimeric polypeptide and the fusion partner. Both chemical and enzymatic cleavable sites are known in the art, as described above. Such sites allow ultimate cleavage of the fragment of the invention from its fusion partner.

In an alternative preparation method, the chimeric polypeptide is overexpressed behind an inducible promoter and purified by affinity chromatography using specific anti-chimeric polypeptide antibodies. For example, the monoclonal antibody SM101 is believed to bind to the amino terminus of P.IA that corresponds to fragment 2. SM101 is described in Virji et al., Journal of General Microbiology 133, 2639–2646 (1987). Similarly, monoclonal antibody SM24 is thought to bind the region of P.IB that corresponds to fragment 6. SM24 is described in Heckels et al., Journal of General Microbiology 135, 2269–2276 (1989).

As another alternative, the overexpressed polypeptide may be purified using a combination of ion-exchange, size-exclusion, and hydrophobic interaction chromatography using methods known in the art. These and other suitable methods are described by Marston, "The Purification of Eukaryotic Polypeptides Expressed in *E. coli*" in *DNA Cloning*, D. M. Glover, Ed., Volume III, IRL Press Ltd., England, 1987.

Use of chimeric polypeptides as probes

The chimeric polypeptides of the invention are useful in detecting and preventing diseases caused by gonococcal infection. For example, the proteins may be labelled and used as probes in standard immunoassays to detect antibodies against the proteins in samples, such as in the sera or other bodily fluids of patients being tested for gonorrhea. In general, a chimeric polypeptide is incubated with the sample suspected of containing antibodies to P.IA or P.IB. The polypeptide is labelled either before, during, or after incubation. Detection of labelled polypeptide bound to an antibody in the sample indicates the presence of the antibody. The antibody is preferably immobilized.

Suitable assays for detecting antibodies with polypeptides are known in the art, such as the standard ELISA protocol described by R. H. Kenneth, "Enzyme-Linked Antibody Assay with Cells Attached to Polyvinyl Chloride Plates" in Kennett et al, Monoclonal Antibodies, Plenum Press, N.Y., page 376 (1981). Briefly, plates are coated with a sufficient amount of an antigenic polypeptide to bind detectable amounts of the antibody. After incubating the plates with the polypeptide, the plates are blocked with a suitable blocking agent, such as, for example, 10% normal goat serum. The sample, such as patient sera, is added and titered to determine the endpoint. Positive and negative controls are added simultaneously to quantitate the amount of relevant antibody present in the unknown samples. Following incubation, the samples are probed with goat anti-human Ig conjugated to a suitable label. The presence of anti-polypeptide antibodies in the sample is indicated by the presence of bound label.

For use in immunoassays, the polypeptide or another molecular probe is labelled with radioactive or non-radioactive atoms or molecules. Such labels and methods for conjugating them to proteins are known in the art.

Some examples of useful radioactive labels include $^{32}P$, $^{125}I$, $^{131}I$, and $^3H$. Use of radioactive labels have been described in U.K 2,034,323, U.S. Pat. No. 4,358,535, and U.S. Pat. No. 4,302,204.

Some examples of non-radioactive labels include enzymes, chromophors, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman, Proc. Natl. Acad. Sci., 47, 1981–1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate.

The label may also be conjugated to the probe by attaching a ligand to the probe by a method described above and incubating the conjugate with a labelled receptor for that ligand. Any of the known ligand-receptor combinations is suitable. The biotin-avidin combination is preferred.

For use in immunoassays, the chimeric polypeptides comprising fragments present on P.IA or P.IB described above are used. Equivalent fragments may also be used. Equivalent fragments include substitution, addition and deletion mutations that do not destroy the ability of the polypeptides to detect specific antibodies.

Use of chimeric polypeptides in Vaccines

Since the chimeric polypeptides of the present invention are important for a vital function of *N. gonorrhoeae* and are found in outer membranes, the polypeptides are useful in vaccines for the prevention of diseases caused by gonococcal infections, such as gonorrhea. For this purpose, it is necessary for the polypeptide to produce neutralizing antibodies. Neutralizing antibodies are antibodies that significantly inhibit the growth of and/or kill gonococcal cells in vitro or in vivo. Growth of gonococcal cells is significantly inhibited in vivo if the inhibition is sufficient to prevent or reduce the symptoms of the disease of an infected mammal.

If a polypeptide defines the desired epitopes, but is insufficiently antigenic, it may be conjugated to a carrier molecule to increase antigenicity or half life. Some suitable carrier molecules include keyhole limpet hemocyanin, Ig sequences, TrpE and human or bovine serum albumin. Conjugation may be carried out by methods known in the art. One such method is to combine a cysteine residue of the fragment with a cysteine residue on the carrier molecule. Alternatively, the carrier molecule may be joined to the polypeptides of the invention by recombinant means, such as those described above. Antigens may also be cross-linked to self to form polymeric antigens or concatamers.

In addition, delivery of the chimeric porin fragments may be effected by means of incorporation into pilin or flagellin sequences as in the prototypical Salmonella delivery system (B. Stocker, Vaccine Vol. 6 (1988)). Expression by means of vaccinia virus vehicles or presentation on BCG bacillus vehicles is also possible (WHO Meeting, Geneva, June 1989, Vaccine, Vol. 8 (1990)). In each case, the synthetic peptide sequences are presented more profitably to the immune system because of their covalent expression within and at the surface of a larger molecule.

Vaccines comprising the chimeric polypeptides of the invention may be used to inhibit the growth of, or kill, *N. gonorrhoeae*. Preferably, the chimeric polypeptides comprise fragments that are present in P.IA or P.IB proteins. The chimeric polypeptides may also comprise equivalent fragments. Equivalent fragments for this purpose include substitution, addition or deletion mutations that produce neutralizing antibodies in a mammalian host such as in a human host.

The present invention further includes vaccine compositions for immunizing mammals, including humans, against infection by *N. gonorrhoeae*. The vaccines comprise the chimeric polypeptides of the invention or their equivalents and pharmaceutically acceptable media and adjuvants. Equivalents of the chimeric polypeptides are as described above.

The vaccine comprises the antigen in a pharmaceutically acceptable medium. The vaccine may include adjuvants, such as muramyl peptides, and lymphokines, such as interferon, interleukin-1 and interleukin-6. The antigen may be adsorbed on suitable particles, such as aluminum oxide particles, or encapsulated in liposomes, as is known in the art.

Since *N. gonorrhoeae* infects mucosal linings, it is preferable for the vaccine to present the antigen in a way that maximizes the induction of antibodies of the IgA class. The induction of IgA antibodies may be maximized by exposing the antigen to the gut. Therefore, vaccines that expose the chimeric protein of the invention to the gut, such as oral vaccines, are preferred.

In addition, the antigen may be exposed to the gut by presenting the antigen in a liposome or in a viral or bacterial replicating vehicle. Some bacterial replicating vehicles include, for example, salmonella and shigella. Some examples of viral replicating systems include, vaccinia and adenovirus. Alternatively, the antigen may be presented fused to a protein that has an affinity for the gut. Examples of such proteins include, for example, adeno spurs and hepatitis B core antigen.

The invention further includes methods of immunizing host mammals, including humans, with an effective amount of the vaccine compositions described above. The vaccine may be administered to a mammal by methods known in the art. Such methods include, for example, oral, intravenous, intraperitoneal, subcutaneous, or intramuscular administration.

EXAMPLES

Example 1

A. Synthesis of Polypeptides

Oligonucleotide chains were specifically synthesized on a Model 381A Applied Biosystems apparatus utilizing beta-cyanoethyl phosphoramidites as substrate. Synthesized nucleotide oligomers were deprotected and cleaved from resin supports using standard procedures as recommended by the manufacturer. One may utilize any of a variety of oligonucleotide purification cartridges or proceed with HPLC purification and isolation.

Efficient chain extension is possible to obtain the desired oligonucleotides in length of up to 100 bases. Specific hydrogen-bonding complements of these chains may be also synthesized in the proper polarity. Specific terminal restriction enzyme site compatible ends may also be designed to facilitate annealing and cloning by ligation to vectors or other synthetic duplexes.

Approximately 100 ng of a specific oligonucleotide chain is annealed to its complement by heating to 100° C. briefly and allowing to cool slowly to room temperature in a buffer containing 10 mM TRIS HCl pH 7.5, 0.1 mM EDTA.

The 5'OH termini that result from synthesis and deprotection cleavage may be phosphorylated with polynucleotide kinase enzyme and rATP by any of several well known means (see Maniatis et. al., DNA Cloning Manual). Ligation of specific pairs of oligonucleotide duplexes is accomplished by means of restriction enzyme site termini or "sticky-ends" through specifically designed "overhangs" resulting in compatible hydrogen bonded overlaps. The covalent gap 5'-3' bond may be closed by means of DNA ligase enzyme from *E. coli* or bacteriophage in simple buffers. In the case of the latter, such as 10 mMTris.HCl pH 7.5, 10 mMMgCl$_2$, 10 mM DTT, 1 mM rATP at 16° C. incubation for several hours are suitable.

Where large sequences need to be created, pairs or groups of hydrogen bonded duplexes may be mixed and allowed to form a specifically ordered linear structure of total length equal to the length of the individual synthetic duplexes. These are subsequently ligated.

By employing a specific vector or expression vector with suitable compatible restriction site termini, the assembled oligonucleotide structure or mini-gene may be easily and directly cloned and expressed as protein.

An example is given below wherein six individual oligonucleotide chains are mixed and annealed. These are allowed to form a specifically ordered structure which is then ligated and translated as protein information. A high proportion of the recombinant clones thereby generated contain a properly ordered insert segment. Hybridization to specific, individual oligonucleotides labeled with a reporter group may be used to identify clones. The use of asymmetric enzyme termini (two different restriction enzymes) in the vector allows specific directional, in-frame cloning of similar compatible asymmetric termini from the arms of the assembled structure.

This process can be extended to include more members of synthetic sequences to produce larger specific coding arrays. Alternatively, an intermediate structure may be cloned, isolated and used as a substrate for further expansion of synthetic sequences by means of specific restriction enzyme sites previously applied within the coding domain. In this way, a given sequence may be expanded, contracted or otherwise permuted in a directed manner. Specifically, chimeric arrays may be produced and easily analyzed.

In order to express specific polypeptides representing epitopes at interesting protein domains, a controllable protein expression system is employed. These systems may involve the juxtaposition of a promoter to control the amino acid coding sequence as a non-fusion process or may involve the linkage of the chimeric sequences to an existing protein coding sequence that itself is under the regulated control of a plasmid. This is known as a fusion protein system. The non-fusion system can utilize any of several well-known, characterized and available promoters such as trp, trc, tic, tac, lac, $P_L$, etc. Fusion protein systems can involve linkage of chimeric coding sequences to trpE, β-galactosidase, Protein A, maltose binding protein, etc.

As a representative general example, synthetic N. gonorrhoeae Porin sequences chosen from specific domains of Porin P.IA and Porin P.IB strain sequences are chosen. These amino acid sequences, otherwise relatively separated in nature, are converted into E. coli biased codons and chemically synthesized. Multiple oligonucleotide chains may be required to efficiently span the chosen sets of sequences. These are synthesized in such a manner that assembly by annealing is ordered through internal compatible or "sticky" ends. The extreme outside termini may be designed so as to provide or make available termini specific for various restriction enzymes.

Figure 3B:
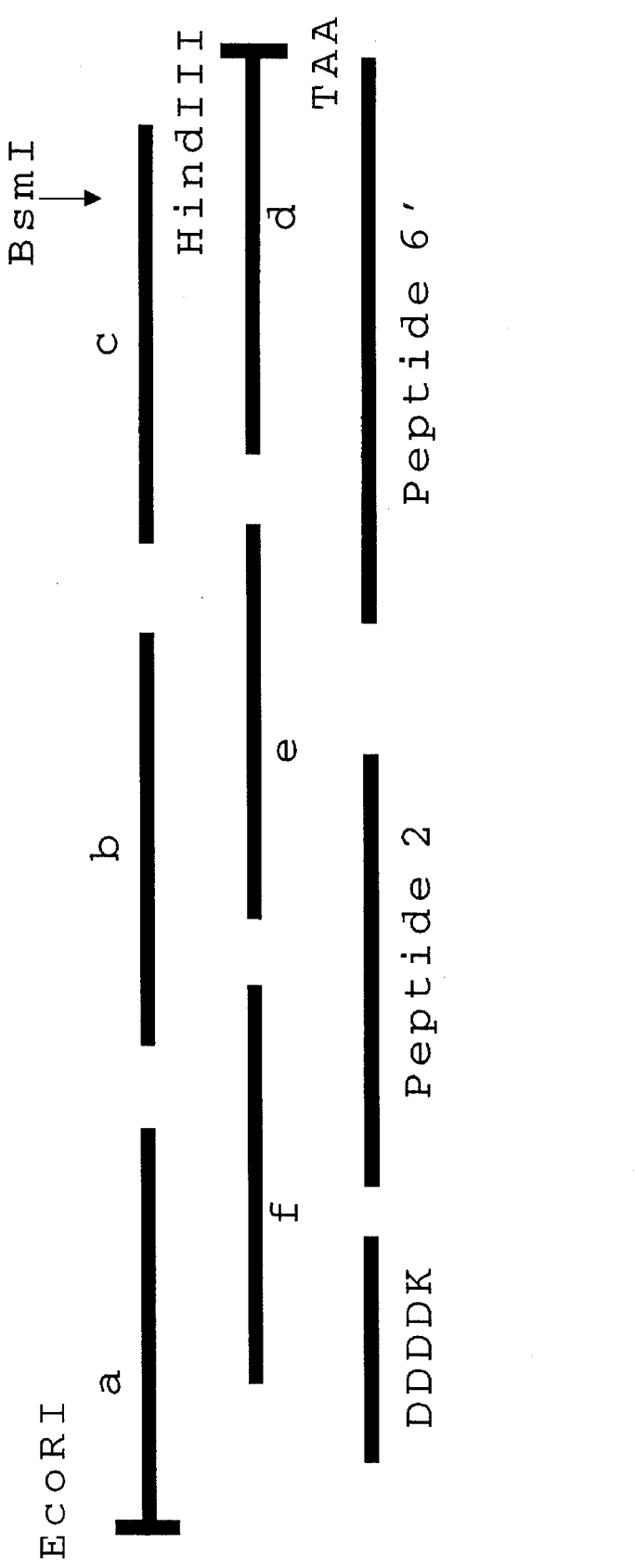
FIG. 3B shows the relationship of oligonucleotides a–f to each other and to the PATH20 restriction sites EcoRI and HindIII in pGC26.
Figure 4B:
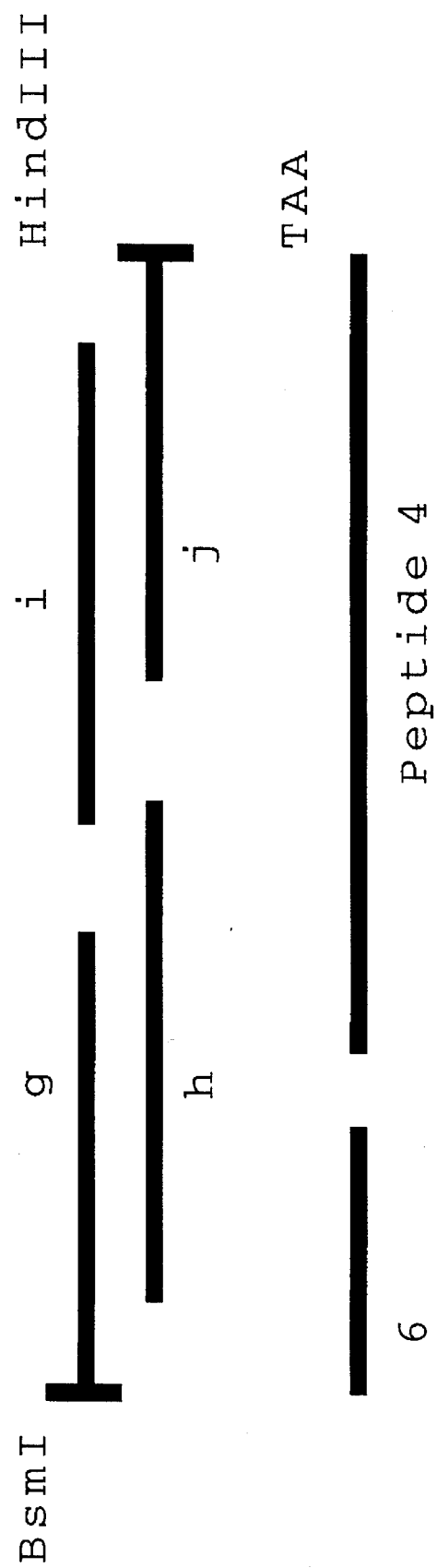
FIG. 4B shows the relationship of oligonucleotides g–j (SEQ ID NOS:10–13) to each other and to the BsmI and HindIII sites of pGC26.

A plasmid that expresses a chimeric polypeptide containing fragments 2 and 6 is called pGC26. To make pGC26, the vector pATH20 is digested at its cloning linker by the enzymes EcoRI and HindIII. PATH20 is a member of the PATH vector systems described by Dieckmann and Tzagoloff in the Journal of Biological Chemistry 260, 1513–120 (1985). The nucleotide sequence of the polylinker in PATH20 (SEQ ID NO:7) is shown in FIG. 2. This polylinker, embedded in the anthranilate synthetase gene or trpE product, makes possible insertion of foreign amino acid coding sequences as "read-through" fusion proteins or chimeric polypeptides. If the proper reading frame triplet codon pattern is identified, the EcoRI site of the vector trpE protein may be joined to the EcoRI site of the synthesized chimeric oligonucelotide. Similarly, the respective HindIII site sequences of the nucleic acids may be annealed and ligated. In the case of pGC26, the six oligonucleotides a–f (SEQ ID NOS:8–9) (see FIG. 3A) are prepared and ligated to each other and to PATH20 at the EcoRI and HindIII sites. The relationship of fragments a–f to each other and to the EcoRI and HindIII sites of PATH 20 is shown in FIG. 3B. The resulting plasmid expresses the trpE protein under the IAA regulated control of the trp promoter and co-expresses the N. gonorrhoeae Porin A/B sequences (fragments 2 and 6) as a co-linear open reading frame carboxy-extension.

This new plasmid, pGC26, expresses a novel protein of molecular weight larger than the native sequence by an increment of N. gonorrhoeae sequence size. Immunologic techniques may be employed to locate and identify individual *N. gonorrhoeae* epitopes and their co-expression with other distinct *N. gonorrhoeae* epitopes. In the case of the Porins, class A and class B sequences may be localized to a single unique protein sequence. In this way, specific combinations of sequences or potential epitopes may be obtained with precision and in useful yield by reproducible methods. Standard techniques may be employed to determine if these proteins are capable of eliciting specific antibody responses, either B or T cell mediated. These antisera would be expected to represent specific responses, in the same animal, to both or all portions or epitopes of the chimeric sequence. These antisera would represent responses to individual epitopes not usually experienced in nature in that particular intertypic combination or display. These antisera may be easily examined to determine whether or not they possess the ability to neutralize or inactivate the parental *N. gonorrhoeae* organisms representative of the individual chimeric epitopes (e.g., Porin A and/or B).

In a similar manner, a hybrid chimeric polypeptide containing a central PIB fragment flanking two PIA amino and carboxy sequences may be constructed from fragments 2, 6 and 4. In the PIA/PIB expressions clone pGC26 (see above), a synthetic chimeric porin sequence is cloned into the pATH20 (SEQ ID NOS:7) polylinker following the trpE sequence at EcoRI and HindIII sites in phase (see FIG. 3B). A unique BsmI recognition sequence is present in oligonucleotide fragment c (FIG. 3A), which represents the carboxy end of the oligonucleotide encoding PIB fragment 6 (SEQ ID NOS:6) (FIG. 1A). Digestion of the original pGC26 plasmid by the restriction enzymes BsmI and HindIII allows additional sequences to be covalently joined, in frame, to existing 2/6 synthetic sequences as extensions.

Thus, amino acid sequence 4 (SEQ ID NOS:4) (FIG. 1A) starting with the amino acid R at position 178 may be added to the carboxy end of GC26 by conjugating pGC26 with BsmI and HindIII in the presence of oligonucleotides g–j (SEQ ID NOS:10–13) (FIG. 4A). The oligonucleotides (g) (SEQ ID NOS:10) 5' CATTCCGAGCCTGTTTGTTTTCGTTCAGTACGCTGGTTTCTAC 3' and (h) (SEQ ID NOS:11) 5' ACGTTTGTAGAAACCAGCGTACTGAACGAAAACAAACAGGCTCGGAATGCT 3', anneal and ligate as above to the oligonucleotide pair (i) (SEQ ID NOS:12) 5' AAACCTCACTCCTACACCACCGAAAAACACCAGGTTCACCGTCTGGTTGGTTA 3' and (j) (SEQ ID NOS:13) 5' AGCTTAACCAACCAGACGGTGAACCTGGTCTTTTTCGGTGGTGTAGGAGTG 3', as well as to pGC26. The relationship of oligonucleotides g–j to each other and to the BsmI and HindIII sites of pGC26 is given schematically in FIG. 4B.

This new clone, when grown and suitably induced to express fusion protein, generates a chimeric polypeptide that is 25 amino acids longer than the pGC26 product described above. This new protein is identifiable by specific reaction in ELISA and western blot with polyclonal anti-*N. gonorrhoeae* sera or monoclonal anti-peptide sera specific for porin A or B regions 2, 6, 4.

Essentially, methods such as described above for the models pGC26 and pGC264 may serve as a means of identifying pertinent cross-serotypic vaccines. All relevant serovars of an otherwise mutually exclusive family of related organisms may thus be tested for neutralization with this novel immunogen. In nature, where a variety of equally infectious but distinct serovars exist, infection may be more efficiently or broadly prevented.

It thereby becomes possible to choose or identify specific amino acid sequences and produce them via synthetic DNA techniques. It is also evident that specific combinations of amino acid sequences may be co-linearly joined and co-expressed as a single complex polypeptide. In this way, sequences from both related and unrelated species or donors may be juxtaposed in a chimeric array. Sequences from related or unrelated serotypes that do not otherwise exchange genetic information at specific loci or "serovaric"

domains may be merged or chimerized (eq A+B=AB or A+B+A=ABA). Where genetic exchange or intertypic exchange is infrequent or not easily detected, specific novel chimeric polypeptides may be created to produce single entities expressing significant epitopes of both strains. This specific directed process may create molecules of immunologic, vaccine or protective significance not easily obtained reproducibly or with high accuracy or specificity in nature. This is particularly significant in the case of the Porin serotypes A and B which, taken together, are believed to represent all varieties of pathogenic *N. gonorrhoeae*, but do not otherwise exist in nature.

Although examples may be found wherein strains in nature, otherwise mutually exclusive, may exchange genetic material, this process is rare and not predictable. The identification and creation of specific sets of sequences from each or several organisms allows specific chimeric epitopes to be created and rapidly tested for clinical significance and utilization as a prophylactic or protective vaccine.

B. Construction of the pGC26 plasmid

The expression plasmid PATH20 (see above) was grown in shake flasks containing Luria Broth and 50 micrograms/ml Ampicillin Sulfate. Supercoiled, covalently closed circular plasmid DNA was isolated by CSCI gradient ultracentrifugation. Approximately 10 micrograms of plasmid was digested to completion with the restriction enzymes EcoRI and HindIII, each of which cleave the vector once. Such cleavage interrupts the TrpE gene (anthranilate synthetase) coding region and creates "sticky end" termini which may be used to accept heterologous DNA sequences, in reading frame, and create chimeric nucleotides following ligation and selection. The enzymes EcoRI and HindIII were added to a 100 ul reaction volume, at 10 units each, containing 50 mMTris-HCl pH7.5, 10 mM mg $Cl_2$, 50 mM NaCl, 10 ug plasmid. The reaction was allowed to proceed for 4 hours at which time digestion was verified by gel electrophoresis. The double digested plasmid DNA was isolated by electroelution from 1% agarose gels and ethanol precipitated. Approximately lug of this plasmid was combined with 200 ng of each of complementary pair of annealled oligonucleotides a/f, b/e and c/d (FIG. 3A). Following ligation, the *N. gonorrhoeae* porin epitope sequences a–f, bounded at their extreme termini by EcoRI and HindIII sites, are produced as shown in FIG. 5. The solution, 100 ul, was brought to 0.3M with NaOAC from a 3M stock and precipitated with ethanol at 0° C. for 1 hour. Following centrifugation in an Eppendorf micro-fuge, the DNA pellet was dried in a Savant Speed-Vac under reduced pressure. The pellet was resuspended in 17 ul water and 2 ul 10×Ligase buffer (60 mMTris pH7.6, 66 mMMg $Cl_2$, 0.2M DTT) with a final ATP concentration of 1 mM. T4 induced DNA ligase (1 ul) was added and the reaction incubated at 16° C. for 12 hours.

To produce ampicillin resistant HB101 colonies bearing recombinant plasmids, 100 ul competent *E. coli* cells were mixed, on ice, with 5 ul of the ligated mixture. The cells and DNA were held, on ice, for 30 minutes, pulsed at 42° C. for 2 minutes and shaken at 37° C. for 30 minutes with 1 ml Luria Broth without antibiotics. An aliquot (100 ul) was spread onto ampicillin agar plates and allowed to incubate at 32° C. overnight. Colonies produced were hybridized versus $P_{32}$ end-labeled oligonucleotides representing the chimeric or individual porin "epitope" sequences of interest. In this way, colonies that represented successful ligation events were rapidly chosen and expanded for analysis.

Aliquots of induced and non-induced (in this case IAA) colony growths, as well as negative control host *E. coli* were lysed and examined by Coumassie blue gel staining and Western blot versus specific porin or carrier protein (TrpE) antisera. Finally, recombinant chimeric epitope expressors were fully sequenced to verify their integrity.

In order to express protein produced by the recombinant porin constructions, cultures bearing plasmids were grown to Abs. 600 nm of approximately 0.2–0.4 in M9 media containing 50 ug/ug ampicillin. Indole acrylic acid (IAA) was added (10 mg/liter) and the culture shaken at least 5 hours or grown overnight for 8–16 hours. Cells were pelleted and resuspended in 25 ml TEN buffer (50 mMTris 7.5, 0.5 mMEDTA, 0.3M NaCl). Lysozyme was added to 0.1 mg/ml. The protease inhibitors PMSF and Aprotinin were added to 1 mM and 10 ug/ml respectively. NP-40 was added to 0.2% final concentration and the lysate held at 0° C. for 10 minutes. When the viscosity had increased, MgCl2 was added to 10 mM and DNAase 1 added to 1 ug/ml. When the viscosity had decreased, the suspension was centrifuged at 4000×g for 15 minutes at 4° C. and the supernatant discarded. The insoluble pellet was washed 1× X with cold TEN and recentrifuged to recover the pellet. This material is highly enriched with recombinant fusion protein and is very suitable for gel electrophoresis, ELISA, Western blot or other immunologic analysis such as animal injection. Recombinant products may be detected by means of specific reactivity of the carrier and/or the ligand sequence by any of the above methods.

The nucleotide sequence obtained as well as the corresponding open reading frame is shown in FIG. 4. This sequence has an enterokinase cleavage site after the first lysine residue (amino acid 7). GC26, which is a chimera of fragments 2 and 6, results from enterokinase cleavage. Enterokinase may be obtained commercially from Sigma Chemical Company, St. Louis Mo. Methods of Cleaving proteins with enterokinase are known in the art. For example, one may use the procedure recommended by the manufacturer or by Hopp et al., Biotechnology 6, 1204–1210 (1988).

Other recombinants are produced and examined by this process and utilized in vaccine candidate analysis procedures.

Example 2

Production of anti-GC26 antisera

Mice are hyperimmunized with GC-30 to show the efficacy of the chimeric polypeptide to induce an anti-P.IA and anti-P.IB humoral response. Bacterial cells containing the construct are washed and lysed in a buffer containing Triton X-100 and sodium deoxycholate. The protein concentration is determined and 100 mg of the chimeric polypeptide or PATH vector alone is injected into female Balb/C mice (8–10 weeks old). The initial injection mixture contains complete Freund's adjuvant. The animals receive a second injection of 100 mg at 7 days with incomplete Freund's adjuvant and a final injection of 100 mg at day 21. Seven days after the last injection, the animals are bled from the retro-orbital socket of the eye, and the sera isolated by centrifugation.

The titer of the anti-P.IA and P.IB humoral response is determined by ELISA. Microtiter plates (96 well) are coated with purified P.IA or P.IB and blocked with 10% new born calf serum in phosphate buffered saline, pH 7.2(NB-10). The sera is serially diluted in NB-10 and added to the plates. After a two hour incubation at 37° C., the plates are washed with saline and probed with goat anti-mouse Ig conjugated to horseradish peroxidase. Following a one hour incubation at 37° C. the plates are washed and binding determined by the addition of a suitable chromogen. The color intensity is determined in an ELISA plate reader at the appropriate wavelength.

Alternatively, the production of anti-GC26 antisera could be accomplished by immunizing mice with affinity purified Trp-GC-26. This can be done using an immuno-affinity column using an anti-TrpE monoclonal antibody to bind the construct. The polypeptide can be diluted from the column using a glycine buffer, pH 2.5. The purified material is used to immunize mice as described above.

---

We claim:

1. A polypeptide that is non-toxic in *E. coil* wherein the polypeptide comprises a sequence of P.IA of *N. gonorrhoeae* wherein the sequence is limited to that which is set forth in SEQ ID NO:2 and a sequence of P.IB of *N. gonorrhoeae* wherein the sequence is limited to that which is set forth in SEQ ID NO:5.

2. A polypeptide that is non-toxic in *E. coli* wherein the polypeptide comprises a sequence of P.IA of *N. gonorrhoeae* wherein the sequence is limited to that which is set forth in SEQ ID NO:2 and a sequence of P.IB of *N. gonorrhoeae* wherein the sequence is limited to that which is set forth in SEQ ID NO:6.

3. A polypeptide according to claim 1 or 2 wherein the polypeptide is fused to a carrier peptide.

4. A polypeptide according claim 3 wherein the carrier peptide is separated from the polypeptide by a cleavable site.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Neisseria gonorrheae
        ( B ) STRAIN: FA19

( v i i ) IMMEDIATE SOURCE:
        ( B ) CLONE: P.IA fragment 1

( x i ) SEQUENCE DESCRIPTION: SEQ ID NO:1:

```
Asp Val Thr Leu Tyr Gly Thr Ile Lys Ala Gly Val Glu Thr Ser Arg
1               5                   10                      15

Ser Val Ala His His Gly Ala Gln Ala Asp
                20              25
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( D ) TOPOLOGY: linear ( v ) FRAGMENT TYPE: internal ( v i ) ORIGINAL SOURCE:
        ( A ) ORGANISM: Neisseria gonorrheae
        ( B ) STRAIN: FA19

( v i i ) IMMEDIATE SOURCE:
        ( B ) CLONE: P.IA fragment 2

( x i ) SEQUENCE DESCRIPTION: SEQ ID NO:2:

```
Val Glu Thr Ser Arg Ser Val Ala His His Gly Ala Gln Ala Asp Arg
1               5                   10                      15

Val Lys Thr Ala Thr Glu Ile Ala Asp
                20              25
```

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( D ) TOPOLOGY: linear ( v ) FRAGMENT TYPE: internal (v i) ORIGINAL SOURCE:
    (A) ORGANISM: Neisseria gonorrheae
    (B) STRAIN: FA19

(v i i) IMMEDIATE SOURCE:
    (B) CLONE: P.IA fragment 3

(x i) SEQUENCE DESCRIPTION: SEQ ID NO:3:

Asp Thr Gly Gly Phe Asn Pro Trp Glu Gly Lys Ser Tyr Tyr Leu Gly
1               5                   10                  15

Leu Ser Asn Ile Ala Gln Pro Glu Glu Arg His Val
            20              25

(2) INFORMATION FOR SEQ ID NO:4:

(i) SEQUENCE CHARACTERISTICS:
        (A) LENGTH: 25 amino acids
        (B) TYPE: amino acid
        (D) TOPOLOGY: linear (v) FRAGMENT TYPE: internal (v i) ORIGINAL SOURCE:
        (A) ORGANISM: Neisseria gonorrheae
        (B) STRAIN: FA19

(v i i) IMMEDIATE SOURCE:
        (B) CLONE: P.IA fragment 4

(x i) SEQUENCE DESCRIPTION: SEQ ID NO:4:

Phe Val Gln Tyr Ala Gly Phe Tyr Lys Arg His Ser Tyr Thr Thr Glu
1               5                   10                  15

Lys His Gln Val His Arg Leu Val Gly
            20              25

(2) INFORMATION FOR SEQ ID NO:5:

(i) SEQUENCE CHARACTERISTICS:
        (A) LENGTH: 27 amino acids
        (B) TYPE: amino acid
        (D) TOPOLOGY: linear (v i) ORIGINAL SOURCE:
        (A) ORGANISM: Neisseria gonorrheae
        (B) STRAIN: MS11

(v i i) IMMEDIATE SOURCE:
        (B) CLONE: P.IB fragment 5

(x i) SEQUENCE DESCRIPTION: SEQ ID NO:5:

Gly Ala Ile Lys Ala Gly Val Gln Thr Tyr Arg Ser Val Glu His Thr
1               5                   10                  15

Asp Gly Lys Val Ser Lys Val Glu Thr Gly Ser
            20              25

(2) INFORMATION FOR SEQ ID NO:6:

(i) SEQUENCE CHARACTERISTICS:
        (A) LENGTH: 27 amino acids
        (B) TYPE: amino acid
        (D) TOPOLOGY: linear (v i) ORIGINAL SOURCE:
        (A) ORGANISM: Neisseria gonorrheae
        (B) STRAIN: MS11

(v i i) IMMEDIATE SOURCE:
        (B) CLONE: P.IA fragment 6

(x i) SEQUENCE DESCRIPTION: SEQ ID NO:6:

```
      Gly  Leu  Phe  Gln  Arg  Tyr  Gly  Glu  Gly  Thr  Lys  Lys  Ile  Glu  Tyr  Glu
      1              5                        10                       15

His  Gln  Val  Tyr  Ser  Ile  Pro  Ser  Leu  Phe  Val
                     20                       25
```

( 2 ) INFORMATION FOR SEQ ID NO:7:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: PATH20 POLYLINKER ( x i ) SEQUENCE DESCRIPTION: SEQ ID NO:7:

```
ATTGAGATCC  CCCCGAATTG  GGAATTCGAG  CTCGGTACCC  GGGGATCCTC  TAGAGTCGAC        60

CTGCAGGCAT  GCAAGCTT                                                         78
```

( 2 ) INFORMATION FOR SEQ ID NO:8:

( i ) SEQUENCE CHARACTERISTICS:
        ( A ) LENGTH: 181 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: GC26 SYNTHETIC DNA ( x i ) SEQUENCE DESCRIPTION: SEQ ID NO:8:

```
AATTCGATGA  TGACGATAAA  GTGGAAACCT  CCCGCTCCGT  GGCGCACCAT  GGCGCGCAGG        60

CGGATCGCGT  TAAAACCGCG  ACCGAAATTG  CGGATCTGGG  CCTGTTCCAG  CGCTACGGCG       120

AAGGCACCAA  AAAAATTGAA  TACGAACATC  AGGTTTATAG  CATTCCGAGC  CTGTTTGTTT       180

A                                                                          181
```

( 2 ) INFORMATION FOR SEQ ID NO:9:

( i ) SEQUENCE CHARACTERISTICS:
        ( A ) LENGTH: 182 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: GC26 SYNTHETIC DNA ( x i ) SEQUENCE DESCRIPTION: SEQ ID NO:9:

```
AGCTTAAACA  AACAGGCTCG  GAATGCTATA  AACCTGATGT  TCGTATTCAA  TTTTTTTGGT        60

GCCTTCGCCG  TAGCGCTGGA  ACAGGCCCAG  ATCCGCAATT  TCGGTCGCGG  TTTTAACGCG       120

ATCCGCCTGC  GCGCCATGGT  GCGCCACGGA  GCGGGAGGTT  TCCACTTTAT  CGTCATCATG       180

CG                                                                         182
```

( 2 ) INFORMATION FOR SEQ ID NO:10:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: GC264 SYNTHETIC DNA ( x i ) SEQUENCE DESCRIPTION: SEQ ID NO:10:

CATTCCGAGC CTGTTTGTTT TCGTTCAGTA CGCTGGTTTC TAC 43

( 2 ) INFORMATION FOR SEQ ID NO:11:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: GC264 SYNTHETIC DNA ( x i ) SEQUENCE DESCRIPTION: SEQ ID NO:11:

ACGTTTGTAG AAACCAGCGT ACTGAACGAA AACAAACACG CTCGGAATGC T 51

( 2 ) INFORMATION FOR SEQ ID NO:12:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: GC264 SYNTHETIC DNA ( x i ) SEQUENCE DESCRIPTION: SEQ ID NO:12:

AAACCTCACT CCTACACCAC CGAAAAACAC CAGGTTCACC GTCTGGTTGG TTA 53

( 2 ) INFORMATION FOR SEQ ID NO:13:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: GC264 SYNTHETIC DNA ( x i ) SEQUENCE DESCRIPTION: SEQ ID NO:13:

AGCTTAACCA ACCAGACGGT GAACCTGGTC TTTTTCGGTG GTGTAGGAGT G 51

( 2 ) INFORMATION FOR SEQ ID NO:14:

( i ) SEQUENCE CHARACTERISTICS:
        ( A ) LENGTH: 182 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: GC26 SYNTHETIC DNA ( x i ) SEQUENCE DESCRIPTION: SEQ ID NO:14:

AATTCGATGA TGACGATAAA GTAGAAACTT CCCGCTCCGT AGCTCACCAT GGAGCTCAGG 60

CGGATCGCGT TAAAACCGCT ACCGAAATCG CTGATTTGGG CTTGTTCCAA AGATACGGCG 120

AAGGCACTAA AAAAATCGAA TACGAACATC AAGTTTATAG TATCCCAGCC TGTTTGTTTA 180

AA 182

( 2 ) INFORMATION FOR SEQ ID NO:15:

( i ) SEQUENCE CHARACTERISTICS:
        ( A ) LENGTH: 183 base pairs ( B ) TYPE: nucleic acid
( C ) STRANDEDNESS: double
( D ) TOPOLOGY: linear ( v i i ) IMMEDIATE SOURCE:
( B ) CLONE: GC26 SYNTHETIC DNA ( x i ) SEQUENCE DESCRIPTION: SEQ ID NO:15:

```
AGCTTTTAAA  CAAACAGGCT  GGGGATACTA  TAAACTTGAT  GTTCGTATTC  GATTTTTTTA      60
GTGCCTTCGC  CGTATCTTTG  GAACAAGCCC  AAATCAGCGA  TTTCGGTAGC  GGTTTTAACG     120
CGATCCGCCT  GAGCTCCATG  GTGAGCTACG  GAGCGGGAAG  TTTCTACTTT  ATCGTCATCA     180
TCG                                                                        183
```